US009616398B2

(12) United States Patent
Chien et al.

(10) Patent No.: US 9,616,398 B2
(45) Date of Patent: Apr. 11, 2017

(54) STIRRING DEVICE AND GEAR TRAIN

(71) Applicant: Taiwan Advanced Nanotech Inc., Taoyuan County (TW)

(72) Inventors: Chien-Hsing Chien, Taoyuan County (TW); Yu-Sheng Yang, Taoyuan County (TW); Jing-Ru Huang, Taoyuan County (TW)

(73) Assignee: TAIWAN ADVANCED NANOTECH INC., Taoyuan (TW)

( * ) Notice: Subject to any disclaimer, the term of this patent is extended or adjusted under 35 U.S.C. 154(b) by 0 days.

(21) Appl. No.: 14/466,005

(22) Filed: Aug. 22, 2014

(65) Prior Publication Data

US 2015/0283524 A1    Oct. 8, 2015

(30) Foreign Application Priority Data

Apr. 2, 2014    (TW) .............................. 103112254 A

(51) Int. Cl.
| | |
|---|---|
| *B01F 7/00* | (2006.01) |
| *B01F 13/08* | (2006.01) |
| *B01F 13/10* | (2006.01) |
| *B01F 15/00* | (2006.01) |
| *G01N 35/00* | (2006.01) |
| *F16H 35/18* | (2006.01) |
| *F16H 1/22* | (2006.01) |

(52) U.S. Cl.
CPC .......... *B01F 13/0845* (2013.01); *B01F 7/005* (2013.01); *B01F 13/1022* (2013.01); *B01F 15/00454* (2013.01); *F16H 35/18* (2013.01); *G01N 35/0098* (2013.01); *B01F 2215/0036* (2013.01); *F16H 1/22* (2013.01); *G01N 2035/00514* (2013.01); *G01N 2035/00534* (2013.01); *Y10T 74/19642* (2015.01)

(58) Field of Classification Search
CPC ........................................................ B01F 7/005
USPC .............................. 261/85, 87; 366/245, 252
See application file for complete search history.

(56) References Cited

U.S. PATENT DOCUMENTS

| | | | | | |
|---|---|---|---|---|---|
| 75,842 | A | * | 3/1868 | Bell .................... | B01F 3/04531 |
| | | | | | 261/87 |
| 325,530 | A | * | 9/1885 | Gore ................... | B01F 3/04539 |
| | | | | | 261/87 |
| 705,361 | A | * | 7/1902 | Klein .................. | B01F 3/04539 |
| | | | | | 261/87 |
| 1,021,401 | A | * | 3/1912 | Fay ....................... | B01F 3/1221 |
| | | | | | 261/87 |

(Continued)

*Primary Examiner* — David Sorkin
(74) *Attorney, Agent, or Firm* — Birch, Stewart, Kolasch & Birch, LLP

(57) ABSTRACT

The present invention provides a stirring device and gear train, the stirring device comprises at least one gear; at least one stirring tube; and at least one connecting portion connecting the gear and the stirring tube. Wherein the gear, the connecting portion, and the stirring portion are hollow, and the gear rotates the stirring tube via the connecting portion. Stirring is performed by utilizing the gear and the stirring tube in the stirring device of the present invention. Not only does the biggest flux be achieved per area, but the problem about cross contamination can also be reduced. In addition, in the gear train, the collimation of the stirring device can be increased by a specific hollow gear and a lengthened hollow bearing train forth in the gear train.

15 Claims, 8 Drawing Sheets

(56) References Cited

U.S. PATENT DOCUMENTS

| | | | | |
|---|---|---|---|---|
| 1,337,732 A | * | 4/1920 | Stoller | F16H 49/005 |
| | | | | 310/103 |
| 2013/0126436 A1 | * | 5/2013 | Ok | B03C 1/30 |
| | | | | 210/695 |

* cited by examiner

STIRRING DEVICE AND GEAR TRAIN

BACKGROUND OF THE INVENTION

Field of the Invention

The present invention relates to a stirring device and a gear train. In particular, it relates to a stirring device including a hollow gear and a hollow gear train.

Description of the Related Art

Commercial available stirring devices have several categories, such as magnetic stirrers, vibration stirrers, and the like, which used for stirring the solution or reagent, and accelerating solute to dissolve into the solution or preventing solidification.

The magnetic stirrer is a lab apparatus used for stirring liquids by a magnetic stirrer rotating rapidly, thereby stirring the solution. Since most chemical reactions could be conducted in a glass beaker, and the material, such as glass, does not shield the magnetic field, the stirrer could work out in the glass beaker. Also, since the stirrer is limited in sizes (the stirrer has various types and sizes), the disadvantage of the stirrer is that it was merely applied in relatively smaller experiments (the solution volume is smaller than 4 liter). However, when it applies in a big volume solution and a viscosity liquid, the magnetic device cannot exhibit good performance, and a conventional mechanical stirring device is needed. In addition, the stirring device was usually used in the open type biological or chemical solutions. If the stirrer is contaminated, the biological or chemical reaction may be possibly contaminated.

In addition, the magnetic force could be applied in an automatic magnetic bead operation platform; one of the core skill of the automatic magnetic bead operation platform is attracting the magnetic bead by a magnet. In other words, the permanent magnet or an electromagnet stick was utilized to insert into a stirring tube, such that the magnetic beads are absorbed on the outside wall of the stirring tube that the magnetic pole end of the magnet is located. For analysis, the specimen amount less than 32 at one operation, there are many different types of magnetic devices spread through the market. However, if the amount of specimen is increased, the volume of the apparatus does not meet the needs in the experiment. Moreover, if too many specimens are operated in the limited space, the problem of cross contamination is hard to avoid.

In addition, the mechanism of the stirring device with vibration is performed by transferring the voltage vibration into the piezoelectric ceramic transducer with mechanical vibration, which could be applied in the biological or chemical analysis steps including immobilization, washing, and interaction. The structure of the stirring device with vibration comprises a vibration unit for controlling vibration frequency, a driving part vibrated by the vibration unit, and a stirring unit connected with and driven by the driving part. More than one stirring sticks were set in the stirring unit, and the vibration unit was allowed to generate the specific frequency, such that the speed of stirring and reaction could be increased by the stirring unit driven by the driving part and concisely controlling the vibration frequency, vibration amplitude, and vibration time. However, air may enter into the sample set forth in the stirring device when vibrating, and results in contamination.

Thus, one kind of stirring device for the biological and chemical reaction with high throughput sample analysis and no contamination is need.

SUMMARY OF THE INVENTION

The present invention provides a stirring device and a gear train. The stirring device performs stirring by using the characteristics of rotation, not merely can the biggest flux per unit area be achieved, but the problem of cross contamination also can be reduced. In addition, the collimation of the stirring device is increased by hollow gears and lengthened bearings thereof in the gear train.

Therefore, the present invention provides a stirring device, comprising: at least one gear including a bearing; at least one stirring tube; and at least one connecting portion; wherein one end of the connecting portion connects the bearing, the other end of the connecting portion connects the stirring tube, and the gear rotates the stirring tube via the connecting portion.

In a preferable embodiment, the stirring device may further comprise a motor, and the motor may control the gear via a coupling.

In a preferable embodiment, when a number of the gears are multiple, the gears are adjacent to each other to form at least one row of gear train.

In a preferable embodiment, when the gears are arranged in at least two rows, any two adjacent rows of gears are arranged in a staggered, up-and-down pattern.

In a preferable embodiment, when the gears are arranged in at least two rows, any two adjacent rows of gears are arranged in an identical plane. In addition, the gear is a magnetic gear.

In a preferable embodiment, a number of gears may have identical size or different size.

In a preferable embodiment, the gear included in the gear train may be rotated by being adjacent to each other.

In a preferable embodiment, the stirring device may further comprise a gear box for installing the gear.

In a preferable embodiment, the bearing and the connecting portion are hollow.

In a preferable embodiment, the bearing has a hollow bearing; wherein a length difference between one portion of the bearing and the other portion of the bearing is 5-20 mm, preferably 10-15 mm.

In a preferable embodiment, the stirring tube is a detachable stirring tube.

In a preferable embodiment, an end of the stirring tube is a closed end, and another end of the stirring tube is an open end; wherein the connecting portion inserts into the open end of the stirring tube and combines with the stirring tube.

In a preferable embodiment, the stirring device may further comprise a magnetic stick; wherein the magnetic stick inserts the stirring tube to perform magnetic effect by passing through the bearing of the gear and the connecting portion.

Also, the present invention provides a gear train, comprising: a plurality of gears, wherein each of the gear comprises a bearing, and the gear is hollow such that the bearing pass through the gear, and the plurality of gears are adjacent to each other to form at least one row of gears.

In a preferable embodiment, when the gear trains are arranged in at least two rows, any two adjacent rows of gears are arranged in a staggered, up-and-down pattern.

In a preferable embodiment, when the gears are arranged in at least two rows, any two adjacent rows of gears are arranged in an identical plane, and the gear is a magnetic gear.

In a preferable embodiment, the plurality of gears has identical size or different size.

In a preferable embodiment, the plurality of gears may be rotated by being adjacent to each other.

In a preferable embodiment, the stirring device may further comprise a gear box for installing the gear.

In a preferable embodiment, the bear is hollow; wherein a length difference between a portion of the bearing and the other portion of the bearing is 5-20 mm, preferably 10-15 mm.

Many of the attendant features and advantages of the present invention will becomes better understood with reference to the following detailed description considered in connection with the accompanying drawings.

BRIEF DESCRIPTION OF THE DRAWINGS

The present description will be better understood from the following detailed description read in light of the accompanying drawings, where.

DETAILED DESCRIPTION OF THE PREFERRED EMBODIMENTS

Figure 1A:
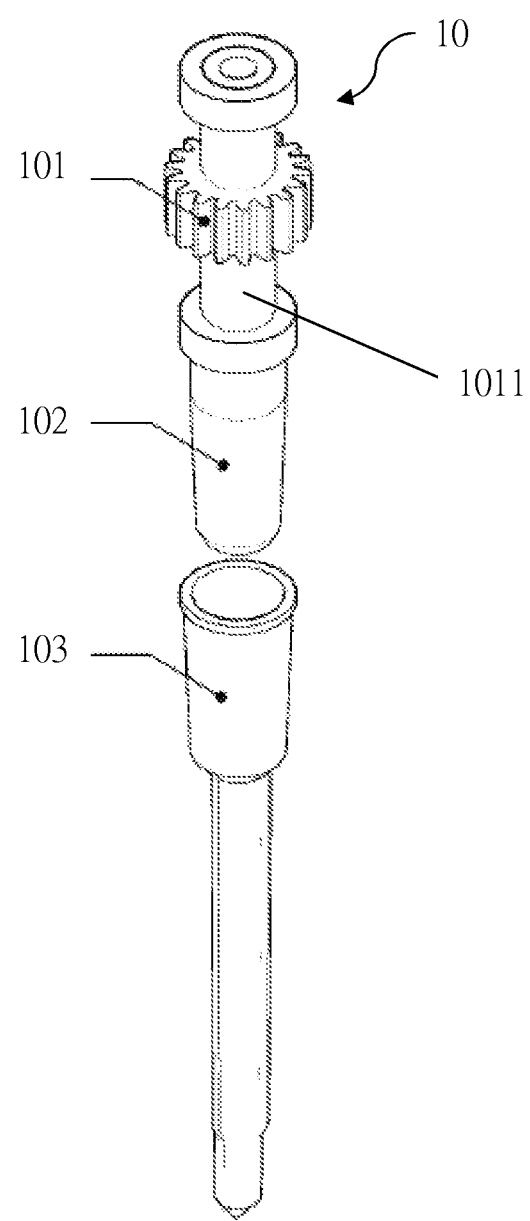
FIG. 1A is a schematic diagram for the main elements of the stirring device in the present invention.

Details of the objects, technical configuration, and effects of the present invention will be described more fully hereinafter with reference to the accompanying drawings, in which exemplary embodiments of the invention are shown. The like reference numerals indicate the like configuration throughout the specification, and in the drawings, the length and thickness of layers and regions may be exaggerated for clarity. The technical content of the present invention will become apparent by the detailed description of the following embodiments and the illustration of related drawings as follows. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The singular forms "a", "and", and "the" are used herein to include plural referents unless the context clearly dictates otherwise.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure is thorough, and will fully convey the scope of the invention to those skilled in the art.

The present invention provides a stirring device and a gear train. The stirring device utilizes a motor to drive a hollow gear train to allow a stirring tube rotating, such that the function of stirring is achieved. Not merely can the biggest flux be achieved per unit area, but the problem of cross contamination also can be solved. In addition, the collimation of the stirring device is increased by hollow gears and lengthened bearings thereof in the gear train.

FIG. 1A is a schematic diagram for the main elements of the stirring device in the present invention. Please refer to FIG. 1A, the present invention provides a stirring device 10, comprising at least one gear 101, at least one connecting portion 102, and at least one stirring tube 103; wherein the gear 101 comprises a hollow bearing 1011 passing through the gear 101. Wherein the hollow bearing 1011 can be designed as a non-hollow bearing or other geometric variant according to the user's requirements. Furthermore, the material of gear 101 may be a magnetic material with rub resistance characteristics, a metal material with rub resistance characteristics, or a plastic material with rub resistance characteristics; wherein the magnetic material with rub resistance characteristics comprises a Neodymium ($Nd_2Fe_{14}B$) magnet or a Samarium Cobalt magnet ($SmCo_5$); the metal material with rub resistance characteristics comprises a cast steel or a cast iron; and the plastic material with rub resistance characteristics comprises polyacetal, polycaprolactam, or polytetrafluoroetane etc. The material of connecting portion 102 may be a metal material or a plastic material; wherein the metal material comprises a cast steel or a cast iron etc, and the plastic material comprises polyacetal, polycaprolactam, or polytetrafluoroetane etc. The main material of stirring tube 103 is a plastic material without shielding magnetic field; wherein the plastic material comprises polypropylene, polycarbonate, polystyrene, or polyethylene.

Figure 1B:
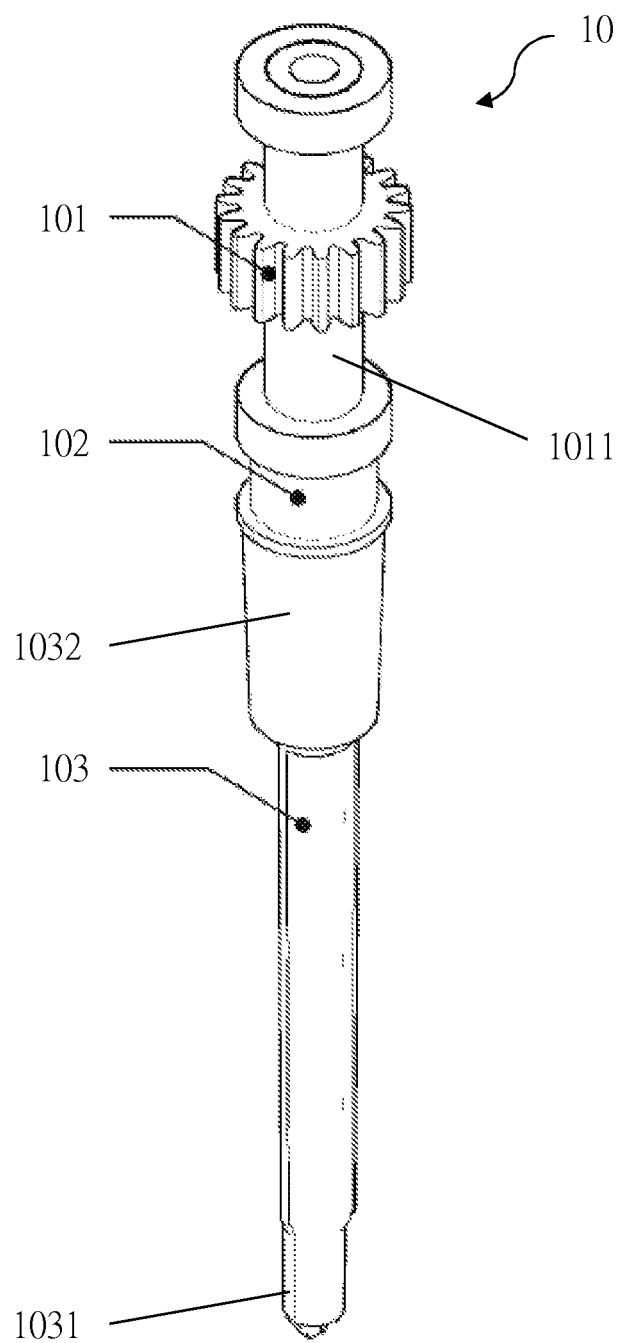
FIG. 1B is a schematic diagram for the combination of the main elements of the stirring device in the present invention.

FIG. 1B is a schematic diagram for combination of the main elements of the stirring device in the present invention. Please refer to FIG. 1B, one end of the connecting portion 102 connects with the hollow bearing 1011, and the other end of the connecting portion 102 connects with the open end 1032 of the stirring tube 103, and the gear 101 and the connecting portion 102 are hollow. The concrete connection method is that insert the hollow bearing 1011 of the gear 101 to and combine with one end of connecting portion 102, and the other end of the connecting portion 102 inserts into the open end 1032 of the stirring tube 103 to combine with it. Thus, the gear 101 can drive the stirring tube 103 by the hollowing bearing 1011 connected with the connecting portion 102 to achieve the function of stirring. One of the embodiments used for the stirring tube 103 of the present invention is a detachable tube, and an end of the stirring tube 103 is a closed end 1031, and the other end of the stirring tube 103 is an open end 1032. The open end 1032 of the stirring tube 103 allows the connecting portion 102 to insert it and combine with each other. The advantage of the stirring device is that a consumable, such as the stirring tube 103, can be replaced quickly and automatically to ensure its collimation. In addition, the consumable can also automatically insert into and withdraw from the connecting portion 102 when using, the conventional operation of the stirring device can be simplified, and the contamination in samples can be reduced.

Figure 1C:
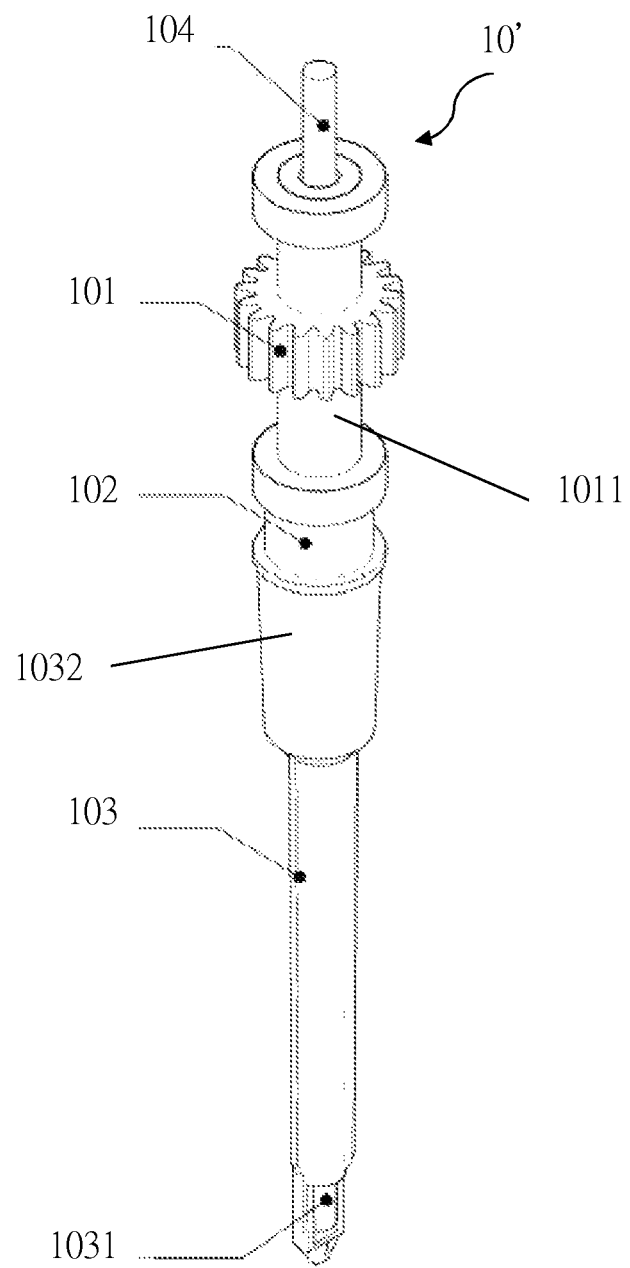
FIG. 1C is a schematic diagram for the elements of another embodiment of the stirring device in the present invention.
Figure 1D:
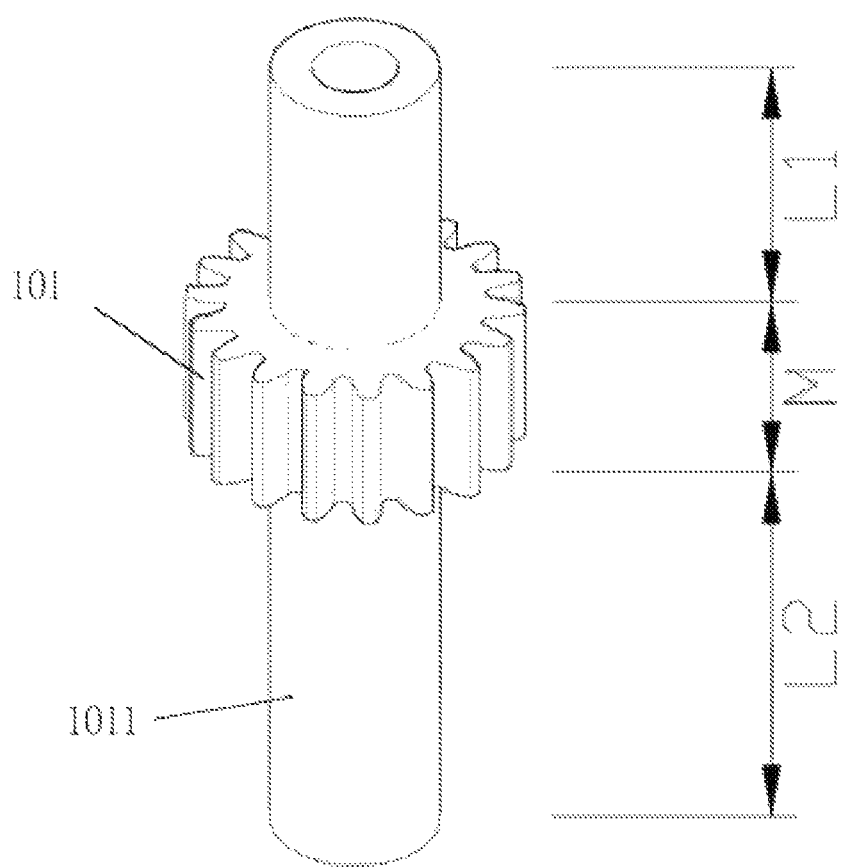
FIG. 1D is a schematic diagram for a hollow gear and a bearing in the present invention.

FIG. 1C is a schematic diagram for the elements of another embodiment of the stirring device in the present invention. Please refer to FIG. 1C, a stirring device 10' of the present invention may further comprise a magnetic stick 104. When the stirring device 10' of the present invention needs the function of magnetic effect, the magnetic stick 104 is used to pass through the hollow bearing 1011 of the hollow gear 101, the connecting portion 102 and insert into the stirring tube 103 to allow the stirring tube 103 having the function of magnetic effect. In addition, it is noted that FIG. 1D is a schematic diagram for a hollow gear and a bearing in the present invention. To enhance the collimation and friction force of the stirring device in the present invention, one portion of the bearing in length is extended to L2. Accordingly, the length (L) of the extended hollow bearing 1011 means the length difference (L) between one portion of the bearing (L2) and the other portion of the bearing (L1) (L=L2−L1) in FIG. 1D. If the length difference (L) of the hollow bearing 1011 is too short, the stirring tube 103 may fall off because of insufficient friction force. If the length difference (L) of the hollow bearing 1011 is too long, the axle center may deviate when rotating. Thus, the length difference (L) of the hollow bearing 1011 is 5-20 mm, and is preferably 10-15 mm.

Figure 2A:
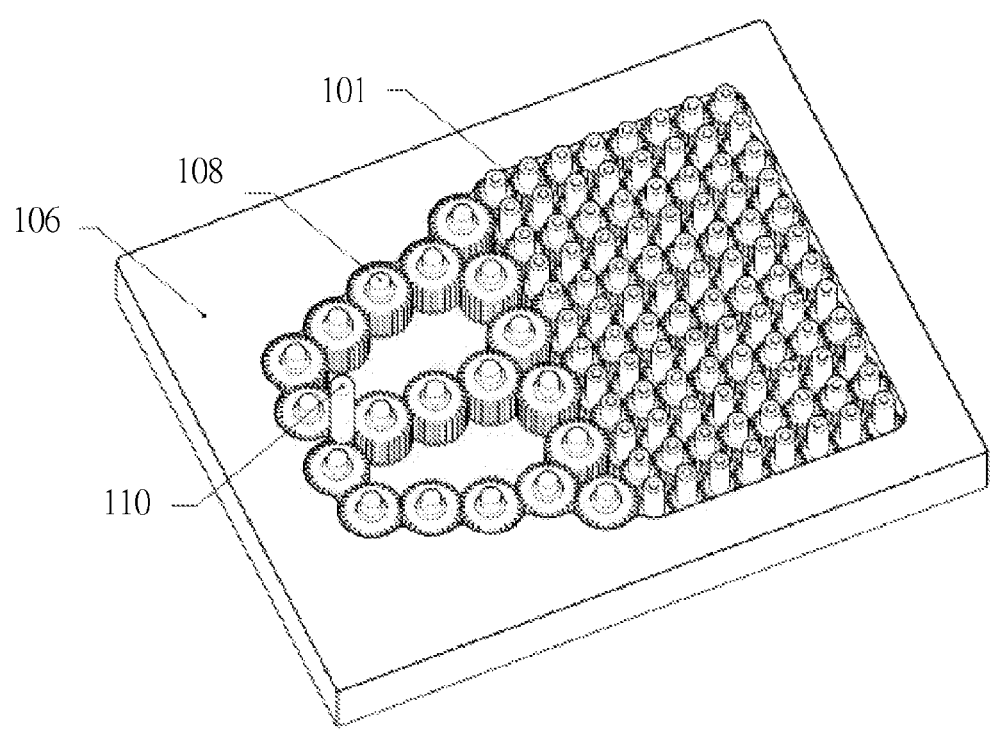
FIG. 2A is a schematic diagram for an embodiment illustrating a gear train in the present invention.
Figure 2B:
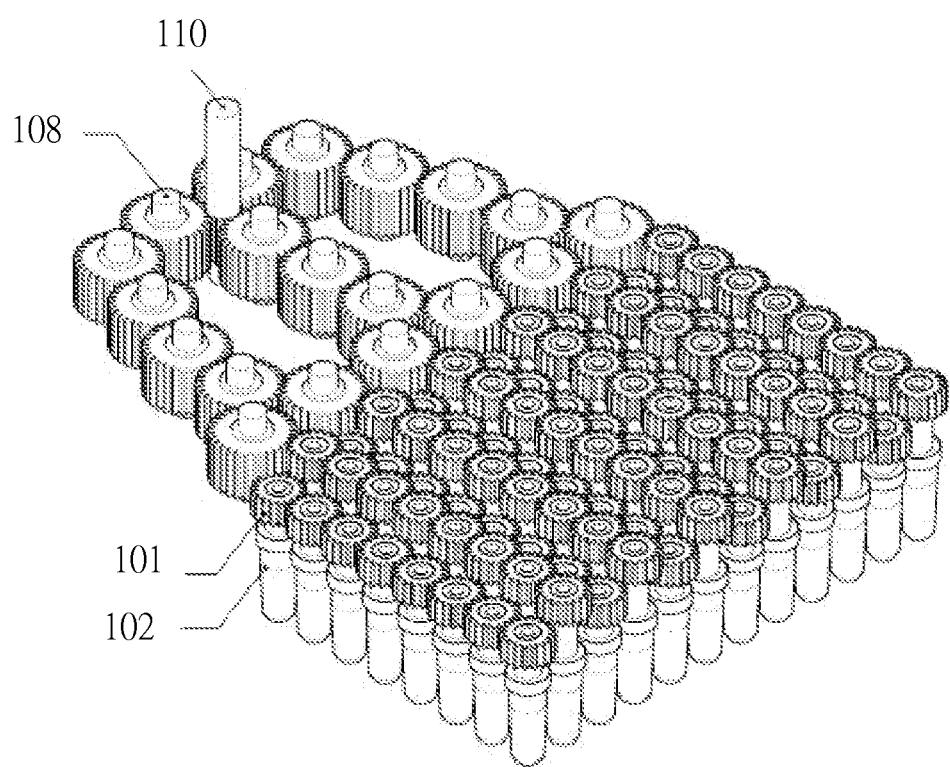
FIG. 2B is a schematic diagram for another embodiment illustrating a gear train in the present invention.

In addition, the present invention further provides a gear train, which is illustrated by FIGS. 2A and 2B. FIG. 2A is a schematic diagram for an embodiment illustrating a gear train in the present invention, and the gear train is arranged in an identical plane. The gear train included in this embodiment comprises a plurality of gears 101; wherein each of the gear 101 comprises a bearing 1011 (not shown), and the plurality of gears 101 are arranged in multiple rows to form a gear train. The plurality of gears 101 included in the gear train may be rotated by being adjacent to each other. When the gears are arranged in at least two rows, any two adjacent rows of gears are arranged in an identical plane, and the gear 101 is a magnetic gear. The advantage of the magnetic gear is that since it has no friction force, the magnetic gear can be arranged and extended without limit. In addition, the gear train can be installed in a gear box 106, and the gear box 106 is designed for partial-open type in this embodiment. However, the present embodiment is merely exemplary, but not limited. For example, the gear box 106 can also be designed for closed-type.

FIG. 2B is a schematic diagram for another embodiment illustrating the gear train in the present invention, and the gear trains are arranged in a staggered, up-and-down pattern. Please refer to FIG. 2B, when the gear trains are arranged in at least two rows, any two adjacent rows of gears 101 are arranged in a staggered, up-and-down pattern. In this arrangement, the gear 101 is driven merely by adjacent gear in the same row rotating relative to each other, this advantage is that the problem of too much net friction force resulted from four sides between all gears 101 contacting in the same plane can be avoided. The suitable material used for this gear arrangement is general one, preferably is the material with rub resistance, such as a metal material or a plastic material; wherein the metal material may comprise a cast steel or a cast iron etc, the plastic material may comprise polyacetal, polycaprolactam, or polytetrafluoroetane etc. Furthermore, a coupling 107 (not shown in FIG. 2B but shown in FIG. 3A) drives a general gear 108 and the gears 101 of the present invention are rotated by an input shaft gear 110 installed in the gear box 106. This driving method is just exemplary, but not limited. For example, the gears arranged side by side, or driven by cross bar etc, may drive the hollow gears 101 rotating in the present invention.

The number, material, arrangement, and driving method of the gear 101 can be adjusted by actual use, but are not limited thereto.

Figure 3A:
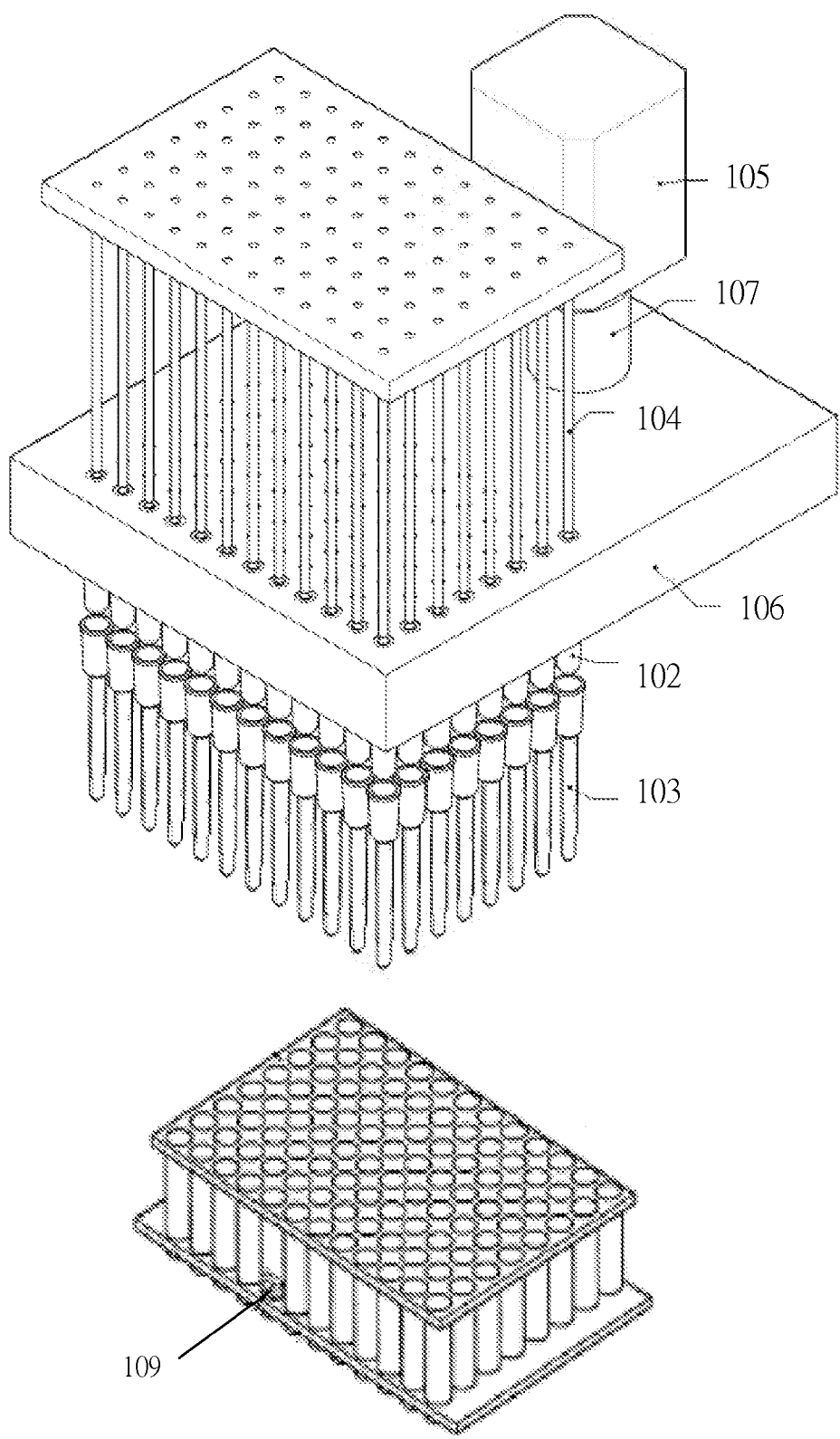
FIG. 3A is a schematic diagram for an embodiment illustrating a stirring device in the present invention.

In addition, FIG. 3A is a schematic diagram for an embodiment illustrating a stirring device in the present invention; wherein the stirring device of the present invention in this embodiment is applied in a sample well 109 (e.g. 96 wells). Please refer to FIG. 3A, the stirring device of the present invention further comprises a motor 105, which controls a gear 101 by a coupling 107, and allows the gears 101 to achieve the function of stirring by a connecting portion 102 driving a stirring tube 103. In addition, the stirring device of the present invention may comprise a gear box 106 used for installing the gears 101. When the magnetic effect is not necessary but general stirring is needed, a magnetic stick 104 can be moved up to above the gear box 106 by a control unit (not shown). The gear 101 is rotated by the motor 105 via controlling the coupling 107, and such that the gear 101 drives the stirring tube 103 to perform the function of stirring by the connecting portion 102. When the magnetic effect is performed, the control unit (not shown) can control the magnetic stick 104 to pass through the hollow bearing 1011 of the hollow gear 101, the connecting portion 102 to insert into the stirring tube 103, such that the stirring tube 103 has the magnetic effect to absorb magnetic beads (not shown) in the sample well 109 (e.g. 96 wells).

Figure 3B:
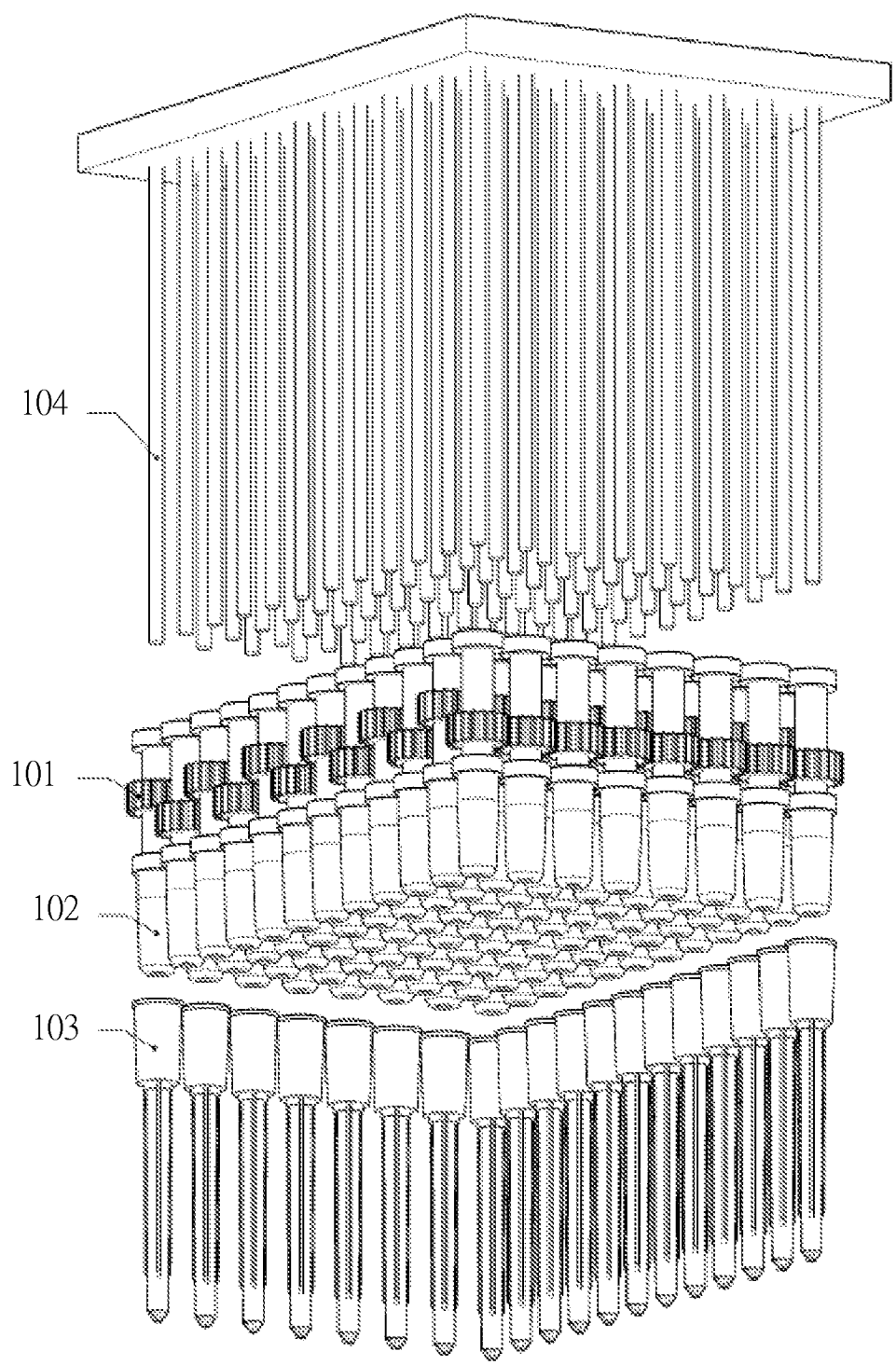
FIG. 3B is a side view for an embodiment illustrating a stirring device in the present invention.

FIG. 3B is a side view for an embodiment illustrating a stirring device in the present invention; wherein when a number of the gears 101 are multiple, the gears are adjacent to each other to form at least one row of gear train; when the gears are arranged in at least two rows, any two adjacent rows of gears are arranged in a staggered, up-and-down pattern. In this embodiment, there are 12 rows of the gears to form gear train (6 rows are set upper, and the other 6 rows are set lower), every two rows are arranged in a staggered, up-and-down pattern. There are 8 gears 101 in each row. The stirring device can insert 96 stirring tubes into 96 connecting portions 102 (only several stirring tubes 103 are shown). The biological or chemical reaction can be simultaneously performed in 96 wells (e.g. sample well 109) by gears driving and rotating relative to each other. In addition, if the magnetic effect is performed, 96 magnetic sticks 104 can also pass through the hollow bearing 1011 of the hollow gear 101 and the connecting portion 102 to insert into the stirring tube 103.

The application of embodiments in the present invention is merely exemplary, but not limited thereto. For example, the number of gears in every row and the number of rows in the gear train may be designed for needs, and the number of magnetic sticks 104 and stirring tubes 103 may be adjusted depending on the number of gears. In addition, the gear 101 of the present invention can be the same or different size, which can be adjusted in light of conditions.

To sum up, the present invention provides a stirring device and a gear train, comprising following advantages:

1. The gear used in the present invention is a hollow gear, which allows the magnetic stick to pass through the connecting portion to insert into the stirring tube to perform the magnetic effect;

2. The gear used in the present invention comprises an extended hollow bearing, such that the collimation of the stirring device is increased;

3. The gear train are arranged in at least two rows, any two adjacent rows of the gears are arranged in a staggered, up-and-down pattern, and the gear is driven merely by adjacent gear in the same row rotating relative to each other, the problem of too much net friction force resulted from four sides between all gears contacting in the same plane can be avoided;

4. The stirring device in the present invention can avoid the problem of cross contamination in the experimental process.

It will be understood that the above description of embodiments is given by way of example only and that various modifications may be made by those with ordinary skill in the art. The above specification, examples, and data provide a complete description of the present invention and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A stirring device, comprising:
   multiple gears arranged in at least two rows, any two adjacent rows of gears being arranged in a staggered, up-and-down pattern;
   a bearing for each gear;
   a stirring tube for each gear; and
   a connecting portion for each bearing and stirring tube;
   wherein one end of the connecting portion connects the bearing, the other end of the connecting portion connects the stirring tube, and the gear rotates the stirring tube via the connecting portion,
   wherein the bearing is configured inside the gear, and
   wherein the bearing and the connecting portion are hollow.

2. The stirring device according to claim 1, further comprising a motor.

3. The stirring device according to claim 2, wherein the motor controls the gear via a coupling.

4. The stirring device according to claim 1, wherein when a number of the gears are multiple, the gears are adjacent to each other to form at least one row of gears.

5. The stirring device according to claim 4, wherein when the gears are arranged in at least two rows, any two adjacent rows of gears are arranged in a staggered, up-and-down pattern.

6. The stirring device according to claim 4, wherein when the gears are arranged in at least two rows, any two adjacent rows of gears are arranged in an identical plane.

7. The stirring device according to claim 6, wherein the gear is a magnetic gear.

8. The stirring device according to claim 4, wherein a number of gears have identical size or different size.

9. The stirring device according to claim 4, wherein the gears are rotated by being adjacent to each other.

10. The stirring device according to claim 1, further comprising a gear box for installing the gear.

11. The stirring device according to claim 1, wherein a length difference between one portion of the bearing on a first side of the gear and the other portion of the bearing on a second opposing side of the gear is 5 to 20 mm.

12. The stirring device according to claim 1, wherein the stirring tube is a detachable stirring tube.

13. The stirring device according to claim 1, wherein the connecting portion inserts into the open end of the stirring tube and combines with the stirring tube.

14. The stirring device according to claim 1, further comprising a magnetic stick.

15. The stirring device according to claim 14, wherein the magnetic stick inserts the stirring tube to perform magnetic effect by passing through the bearing of the gear and the connecting portion.

* * * * *